United States Patent
Cheron et al.

(10) Patent No.: US 6,958,408 B2
(45) Date of Patent: Oct. 25, 2005

(54) LIGANDS WITH AT LEAST A FLUOROSILCONE SUBSTITUENT USEFUL FOR PREPARING METAL-LOCENES

(75) Inventors: Virginie Cheron, Paris (FR); Jean-Luc Couturier, Lyons (FR); Hendrik Hagen, Utrecht (NL); Gerard Van Koten, Den Dolder (NL); Berth Jan Deelman, Kapelle (NL)

(73) Assignee: Total Petrochemicals France, Puteaux (FR)

( * ) Notice: Subject to any disclaimer, the term of this patent is extended or adjusted under 35 U.S.C. 154(b) by 0 days.

(21) Appl. No.: 10/344,528
(22) PCT Filed: Aug. 2, 2001
(86) PCT No.: PCT/FR01/02525

§ 371 (c)(1),
(2), (4) Date: Sep. 2, 2003

(87) PCT Pub. No.: WO02/14337

PCT Pub. Date: Feb. 21, 2002

(65) Prior Publication Data

US 2004/0044235 A1 Mar. 4, 2004

(30) Foreign Application Priority Data

Aug. 18, 2000 (FR) .............................. 00 10724

(51) Int. Cl.⁷ .......................... C07F 17/00; B01J 31/00; C08F 4/44
(52) U.S. Cl. ........................ 556/11; 556/12; 556/478; 556/487; 556/489; 526/127; 526/160; 526/943; 502/103; 502/117
(58) Field of Search .............................. 556/11, 12, 478, 556/487, 489; 502/103, 117; 526/127, 160, 943

(56) References Cited

U.S. PATENT DOCUMENTS

| | | | |
|---|---|---|---|
| 5,631,335 A | 5/1997 | Alt et al. | 526/126 |
| 5,637,744 A | 6/1997 | Alt et al. | 556/12 |
| 5,646,083 A | 7/1997 | Van Beek | 502/104 |
| 5,786,495 A | 7/1998 | Resconi et al. | 556/11 |
| 6,054,404 A | 4/2000 | Resconi et al. | 502/103 |
| 6,180,733 B1 | 1/2001 | Resconi et al. | 526/127 |
| 6,225,425 B1 * | 5/2001 | Dolle et al. | 526/127 |

FOREIGN PATENT DOCUMENTS

| | | |
|---|---|---|
| EP | 0 530 908 A1 | 3/1993 |
| EP | 0 604 908 | 7/1994 |
| EP | 0 628 565 | 12/1994 |
| EP | 0 729 968 | 9/1996 |
| WO | WO 99 54367 | 10/1999 |

OTHER PUBLICATIONS

Jany G. et al., "para–Fluoro benzyl substituted bis (idenyl) metallocenes as catalyst precursors in ethane polymerization", Journal of Organometallic Chemistry, CH, Elsevier–Sequoia S.A. Lausanne, vol. 553, No. 1–2, Feb. 25, 1998; pp. 173–178, XP004204917 ISSN: 0022–328X, p. 174; Figure 1.

* cited by examiner

Primary Examiner—Porfirio Nazario-Gonzalez
(74) Attorney, Agent, or Firm—Smith, Gambrell and Russell, LLP

(57) ABSTRACT

The invention concerns ligands with at least a fluorosilicone substituent of general formulae (I) and (II); a method for preparing them and their use for producing catalysts useful for olefin polymerisation

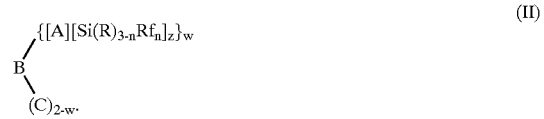

17 Claims, No Drawings

LIGANDS WITH AT LEAST A FLUOROSILCONE SUBSTITUENT USEFUL FOR PREPARING METAL-LOCENES

FIELD OF THE INVENTION

The present invention relates to ligands (of transition metals) with at least one fluorosilicone [sic] substituent, to a process for preparing them and to their use in the preparation of metallocene-type catalysts which can be used in particular for the polymerization of olefins.

BACKGROUND OF THE INVENTION

Veronica Herrera et al. (Inorganic Chemistry Communications, 1998, pages 197 to 199) describe organic complexes of formulae: $[\eta^5$—$C_5H_4CH_2CH_2(CF_2)_9CF_3]Rh$ $(CO)L$ with L=CO or $P[CH_2CH_2(CF_2)_5CF_3]_3$ and $Cl_2Ni\{P[CH_2CH_2(CF_2)_8CF_3]_3\}$, which are obtained from the ligands $C_5H_4CH_2CH_2(CF_2)_9CF_3$ and $P[CH_2CH_2(CF_2)_5CF_3]_3$.

Russell P. Hugues et al. (Organometallics, 1966, 15, pages 286 to 294) showed that it was necessary to have, in ligands of the $\eta^5$—$C_5H_4(CH_2)_n(CF_2)_mF$ type, a hydrocarbon spacer group in order to isolate the cyclopentadienyl ring from the attractive effect of the perfluorinated chains in the above-mentioned ligands.

International Application WO 99/54367 discloses catalytic systems of metallocene type in which the cyclopentadienyl radical always comprises at least one substituent of formula:

$$-\!\!\!+\!\!(CH_2)_s\!\!-\!\!R^2]_r$$

in which $R^2$ represents in particular a fluoroalkyl radical having a number of carbon atoms ranging from 1 to 25, s is an integer ranging from 1 to 20 and r=1, 2, 3, 4 or 5.

DESCRIPTION OF INVENTION

A subject-matter of the invention is compounds of general formulae (I) or [sic] (II):

$$[A][Si(R)_{3-n}Rf_n]_z \quad (I)$$

$$\begin{array}{c}\{[A][Si(R)_{3-n}Rf_n]_z\}_w \\ B \\ (C)_{2-w}\end{array} \quad (II)$$

in which:
- A represents a cyclopentadienyl, indenyl or fluorenyl radical;
- R represents a hydrogen atom, a linear or branched alkyl radical having a number of carbon atoms ranging from 1 to 40, an alkoxy radical having a number of carbon atoms ranging from 1 to 10, an aryl radical having from 6 to 20 carbon atoms, an aryloxy radical having from 6 to 10 carbon atoms or an alkenyl radical having a number of carbon atoms ranging from 2 to 10;
- Rf represents a perfluoroalkyl radical $C_xF_{2x+1}$—$(CH_2)_y$— in which x represents an integer ranging from 1 to 20 and y=0, 1, 2 or 3;
- n=1, 2 or 3;
- z is equal to 1, 2 or 3;
- B represents a divalent group $>MR^1R^2$ or else $$\begin{array}{c} R^1 \;\; R^3 \\ | \;\;\;\; | \\ -C-C- \\ | \;\;\;\; | \\ R^2 \;\; R^4 \end{array}$$

in which M represents a carbon atom, a silicon atom, a germanium atom or a tin atom; $R^1$, $R^2$, $R^3$ and $R^4$, which are identical or different, represent a hydrogen atom, a linear or branched alkyl radical having a number of carbon atoms ranging from 1 to 20 or an aryl radical having from 6 to 14 carbon atoms; preferably, B represents divalent groups such as: —$(CH_2)_2$—, —$CH(CH_3)$—$CH_2$—, —$CH(C_4H_9)C(CH_3)_2$—, —$CH_2Si(CH_3)_2$— or $>Si(CH_3)_2$;

- C represents a cyclopentadienyl, methylcyclopentadienyl, pentamethylcyclopentadienyl, butylcyclopentadienyl, indenyl, naphthyl or fluorenyl radical;
- w=1 or 2.

Preference is given, among the compounds of formulae (I) and (II), to those in the formulae of which A represents a cyclopentadienyl radical, R represents a $CH_3$— and Rf represents a perfluoroalkyl radical $C_xF_{2x+1}(CH_2)_y$— in which x ranges from 1 to 8 and y=0 or 2.

Preferably, Rf=$CF_3(CF_2)_5(CH_2)_2$— or $CF_3(CF_2)_7$—; n=1; z=1 or 2; B=$>Si(CH_3)_2$; and w=2.

Mention will be made, by way of illustration of compounds of formula (I), of:

- dimethyl(1H,1H,2H,2H-perfluoro-1-octyl)silylcyclopentadiene,
- dimethyl(perfluorooctyl)silylcyclopentadiene,
- 1,3-bis[dimethyl(perfluorooctyl)silyl]cyclopentadiene.

Mention will be made, by way of illustration of compounds of formula (II), of the compounds of formula:
$(CH_3)_2Si[C_5H_4Si(CH_3)_2C_8F_{17}]_2$
$(CH_3)_2Si[C_5H_3\{Si(CH_3)_2C_8F_{17}\}_2]_2$ The compounds of formula (I) in the formulae of which y is other than 0 can be prepared according to the following reaction scheme:

[1]
$$[A][Si(R)_{3-n}Rf_n]_{z-1} + BuLi \longrightarrow [A][Si(R)_{3-n}Rf_n]_{z-1}Li + \text{butane}$$
$$1 \qquad\qquad\qquad\qquad 2$$

[2]
$$[A][Si(R)_{3-n}Rf_n]_{z-1}Li + Rf_nSi(R)_{3-n}X \longrightarrow [A][Si(R)_{3-n}Rf_n]_z + LiX$$
$$2 \qquad\qquad\qquad\qquad 3$$

with $Rf=C_xF_{2x+1}(CH_2)_y$—;
X=Cl, Br or I and z=1, 2 or 3.

The reaction (1) is carried out in a known way, which consists in preparing the lithiated derivative 2 in a nonpolar solvent, such as hexane, by reacting 1 with butyllithium at a temperature between 0° C. and 20° C. for several hours. On completion of the reaction, the reaction solvent is removed and then the product obtained is dried under reduced pressure. The reaction is carried out under a nitrogen atmosphere and in the absence of moisture.

As regards the reaction (2), it is carried out according to noncritical conditions, which consist in dissolving the lithiated derivative 2 in an ether, such as THF, at low temperature and then the addition is carried out [sic] to the solution obtained of an ethereal solution of perfluorohaloalkylsilane 3 [sic] maintained at a temperature in the region of 0° C., the said halochlorosilane [sic] preferably being used in a molar excess of 1% to 10% with respect to the stoichiometry of the reaction (2).

The reaction is subsequently continued for several hours at ambient temperature with stirring, the volatile compounds are then removed under reduced pressure and the product (I) obtained is extracted by means of an inert solvent and then distilled under reduced pressure.

Use is preferably made of the perfluoroalkylchlorosilanes $Rf_nSi(R)_{3-n}Cl$, which can be obtained according to a method described in J. Fluorine Chem., 44, page 191, 1955.

The compounds of formula (I) in the formulae of which y=0 can be obtained according to the reactions below:

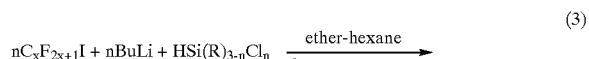  (3)

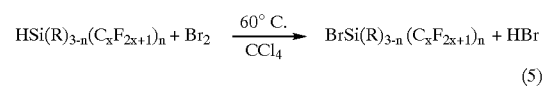  (4)

  (5)

n=1, 2 or 3; z=1, 2 or 3.

The reaction (3) is carried out according to a process which consists in slowly adding a solution of BuLi in hexane to a mixture composed of $C_xF_{2x+1}I$ and of a molar excess of $HSi(R)_{3-n}Cl_n$, with respect to the molar amount of $C_xF_{2x+1}I$ employed, in ether at −78° C.

The compounds of formula (II) can be obtained according to known methods, which consist in reacting the lithiated compounds (I) and/or (C) in a solvent medium with a dichlorinated compound $BCl_2$.

Another subject-matter of the invention is the use of the compounds of formula (I) or (II) as ligands of metals of Group (III) [sic], IVb, Vb or VIb, of the lanthanides or of the actinides of the Periodic Table in the preparation of metallocenes of formulae:

  (III)

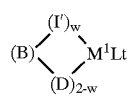 (IV)

in which (B) and w have the same meanings as in the abovementioned formulae (I) and (II);

(I') represents (I) in which the radical (A) has one hydrogen less, (C') represents (C) with one hydrogen less;

D=(C') or (I');

$M^1$ represents a metal from Groups III, IVb, Vb or [sic] VIb and a metal from the group of the lanthanides or actinides;

L, which is identical or different, represents a halogen atom, a linear or branched alkyl radical having a number of carbon atoms ranging from 1 to 20, an alkenyl radical having from 2 to 20 carbon atoms, an alkoxy radical having from 1 to 20 carbon atoms or an aryloxy or aryl radical having from 6 to 40 carbon atoms;

t represents an integer ranging from 1 to 4 and is equal to 2 when, in the formulae (III) and (IV), $M^1$=Ti, Zr or Hf.

Preferably, $M^1$ represents a metal from Group IVb and, very particularly, $M^1$ represents Zr.

The compounds of formula (III) or (IV) can be obtained according to known methods, which consist in introducing the lithiated derivative of (I) or of (II), in solution in an ether, such as THF, dropwise at low temperature into an ethereal solution of $M^1L_t$ at approximately 0° C., then reaction is allowed [sic] to take place at ambient temperature with stirring for several hours and the compounds (III) or [sic] (IV) are isolated [sic] according to methods known to a person skilled in the art.

Another subject-matter of the present invention is a process for the production of polyolefins by polymerization of at least one olefin in the presence of a catalyst which comprises at least one compound of formula (III) or (IV) as precatalyst and at least one cocatalyst.

The polymerization can be a homopolymerization or a copolymerization.

According to the present invention, preference is given to the homopolymerization or the copolymerization of olefins of formula:

$R^\alpha$—CH=CH—$R^\beta$, in which $R^\alpha$ and $R^\beta$, which are identical or different, represent a hydrogen atom, a halogen atom, a linear or branched hydrocarbon radical having a number of carbon atoms ranging from 1 to 20 and preferably ranging from 1 to 10 or a phenyl radical optionally substituted by a halogen atom or a linear or branched alkyl radical having a number of carbon atoms ranging from 1 to 4; $R^\alpha$ and $R^\beta$ can also, together with the atoms connecting them, form one or more rings.

Mention will be made, by way of illustration of such olefins, of 1-olefins, such as ethylene, propylene, 1-butene, 1-pentene, 1-hexene, 1-octene or 4-methyl-1-pentene; styrene; dienes, such as 1,3-butadiene or 1,4-butadiene; or cycloolefins, such as norbornene, tetracyclododecene, norbornadiene or vinylnorbornene.

The polymerization process of the invention applies very particularly to the homopolymerization of ethylene.

The polymerization can be carried out in a known way in the gas phase or in a liquid reaction medium; an inert solvent or the olefin (to be polymerized) can be used as reaction medium.

The polymerization can be a solution, suspension, emulsion or bulk polymerization, a gas-phase polymerization or a polymerization in a supercritical medium ($CO_2$). It can be carried out either continuously or batchwise, at high pressures ranging from 50 to 300 MPa (bar) and at low pressures ranging from 0.01 to 50 MPa. The polymerization can be carried out at temperatures ranging from 0° C. to 250° C. and preferably ranging from 50° C. to 150° C.

The catalyst which comprises at least one compound of formula (III) or (IV) of the present invention can be used in a homogeneous phase or can be supported.

Mention will be made, as support which can be used according to the present invention, of silica gels, fluorinated silica, highly divided polyolefin powder or inorganic oxides, such as alumina or silica.

The catalyst used in the present invention preferably comprises, as precatalyst, a metallocene of formula (III) or (IV) and a cocatalyst. It is possible to use a mixture of at least 2 or more metallocenes (III) or (IV), in particular when a reasonably broad molecular distribution is desired.

Mention will be made, as cocatalyst which can be used according to the present invention, of Lewis acids, such as $BF_3$, organoboron compounds, such as tris(4-fluorophenyl)- borane or tris(pentafluorophenyl)borane, or organoaluminium compounds, such as aluminoxanes, represented by the general formulae for the linear compounds:

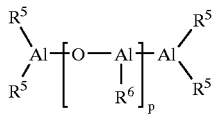 (V)

and for the cyclic compounds:

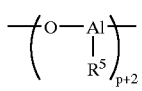 (VI)

in which the $R^5$ radicals, which can be identical or different, represent a hydrogen atom, a linear or branched alkyl radical having a number of carbon atoms ranging from 1 to 20, a fluoroalkyl radical having a number of carbon atoms ranging from 1 to 6, an aryl radical having from 6 to 18 carbon atoms or a fluoroaryl radical having from 6 to 18 carbon atoms and p can be equal to 0 or represents an integer ranging from 1 to 50.

The aluminoxanes are also available commercially. Thus, Aldrich sells, for example, methylaluminoxanes as a 10% by weight solution in toluene.

Use will preferably be made of aluminoxanes in the formulae of which the $R^5$ radicals are identical and represent a methyl, an isobutyl or a phenyl and very particularly a methyl.

The proportions of metallocenes (III) or [sic] (IV) and of cocatalysts constituting the polymerization catalyst can vary to a large extent. A cocatalyst/transition metal $M^1$ molar ratio ranging from 1/1 to 10 000/1 and preferably ranging from 1/1 to 1 000/1 will be used.

The metallocenes (III) or [sic] (IV) of the present invention can be used according to concentrations based on the transition metal $M^1$ which range from $10^{-3}$ to $10^{-8}$ mol, preferably from $10^{-4}$ to $10^{-7}$ mol, of metal $M^1$ per litre of solvent.

The use of the metallocenes (III) and/or (IV) of the present invention in processes for the polymerization of olefins makes it possible to polymerize olefins with a good productive output.

The examples which follow illustrate the invention.

EXAMPLES

The following reactants are used:
cyclopentadiene was obtained by cracking dicyclopentadiene and is distilled before use;
chloro(dimethyl)(1H,1H,2H,2H-perfluoro-1-octyl)silane was obtained according to a process described in J. Fluorine Chem., 44, page 191, 1995;
all the other reactants are commercially available and are used without purification;
the solvents are dried and distilled before their use. The compounds obtained were characterized by elemental analysis and by $^1H$, $^{13}C$, $^{29}Si$ and $^{19}F$ NMR.

All the reactions are carried out under a dry nitrogen atmosphere.

The NMR spectra were recorded on a Varian Inova 300 or Varian Mercury 200 device.

Mass spectrometry (nano ES-Q-TOF-MS) was carried out on a Micromass Q-Tof hybrid tandem mass spectrometer and Mass Lynx software, version 3.0.

Preparation of dimethyl(1H,1H,2H,2H-perfluoro-1-octyl)-silylcyclopentadiene 2.4 ml (29.1 mmol) of freshly distilled cyclopentadiene are added to a solution of n-BuLi (30.4 mmol) in hexane (100 ml), stirred and maintained at 0° C. The reaction mixture obtained is stirred at ambient temperature for 3 hours, the solvent is then removed and the product obtained is washed 3 times with pentane (3×50 ml) and is dried under reduced pressure.

The cyclopentadienelithium obtained is dissolved in 100 ml of THF at −78° C. and the solution is added dropwise over 30 minutes to a solution of $C_6F_{13}C_2H_4Si(CH_3)_2Cl$ (13 g (29.5 mmol) in 100 ml of THF), maintained at 0° C.

The reaction medium is subsequently stirred at ambient temperature for approximately 12 hours. The volatile compounds are removed under reduced pressure. The product is extracted with 100 ml of pentane, dried under reduced pressure and then distilled.

10.94 g of an orangy liquid with a boiling point of 75–80° C. under 0.4 mmHg are obtained (yield: 80% with respect to the cyclopentadiene employed).

$^1H$ NMR (CDCl$_3$) δ (ppm): 6.87 and 6.71 (2×m, CH=, 1- and 2-$C_5H_5SiMe_2R_f$), 6.63 and 6.53 (2×m, CH=, 5-$C_5H_5SiMe_2R_f$), 3.40 (m, 5-CH, 5-$C_5H_5SiMe_2R_f$), 3.04 (m, 5-CH$_2$, 1- and 2-$C_5H_5SiMe_2R_f$), 1.98 (m, CH$_2$—CF$_2$, 1-, 2- and 5-$C_5H_5SiMe_2R_f$), 0.88 (m, CH$_2$—Si, 1 and 2-$C_5H_5SiMe_2R_f$), 0.68 (m, CH$_2$—Si, 5-$C_5H_5SiMe_2R_f$), 0.21 (s, SiMe$_2$, 1- and 2-$C_5H_5SiMe_2R_f$), 0.03 (s, SiMe$_2$, 5-$C_5H_5SiMe_2R_f$).

The complexity of the proton NMR spectrum is due to the presence of the 1-, 2- and 5-(1H,2H,2H,2H-perfluoro-1-octyldimethylsilyl)cyclopentadiene [sic] isomers, it being understood that the 5 isomer is predominant at ambient temperature.

Elemental analysis calculated for $C_{15}H_{15}F_{13}Si$: C: 38.30; H: 3.19; F: 52.55; Si: 5.96. Found: C: 38.08; H: 3.29; F: 52.74; Si: 5.81.

Preparation of 1,1'-bis[dimethyl(1H,1H,2H,2H-perfluoro-1-octyl)silylcyclopentadienyl]zirconium dichloride

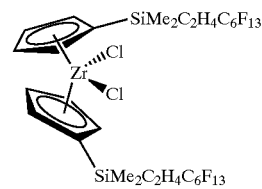

37 g (78.7 mmol) of $C_5H_5Si(CH_3)_2C_2H_4C_6F_{13}$ are added to a solution, stirred and maintained at 0° C., of n-BuLi (78.9 mmol) in hexane (200 ml). The mixture obtained is stirred at ambient temperature for 3 hours. The solvent is subsequently removed and the product is washed with pentane (3×50 ml) and subsequently dried under reduced pressure.

The Li[$C_5H_4Si(CH_3)_2C_2H_4C_6F_{13}$], cooled to −78° C., is dissolved in 100 ml of pre-cooled THF. A solution of 9.08 g (38.2 mmol) of ZrCl$_4$ in 100 ml of THF is prepared according to a method described [lacuna] Journal Am. Chem. Soc., 1995, Vol. 117, page [sic] 12114–12129. The solution of Li[$C_5H_4Si(CH_3)_2C_2H_4C_6F_{13}$] in THF is added dropwise over 30 minutes to the solution of ZrCl$_4$ in THF, cooled to 0° C.

The solution obtained is stirred at ambient temperature for 48 hours. The volatile products are removed under reduced pressure and the residue is extracted with 100 ml of refluxing toluene.

The orange-coloured extract is filtered while hot and then the filtrate is concentrated under reduced pressure. 31.5 g of a product in the form of white needles are obtained (yield: 75% with respect to $ZrCl_4$).

$^1$H NMR (200.14 MHz, $CDCl_3$) δ (ppm): 6.65 and 6.52 (t, 4H, $J_{AX}=J_{AX'}$=2.6 Hz, CH=), 1.98 (m, 2H, $CH_2$—$CF_2$), 0.96 (m, 2H, $CH_2$—Si), 0.37 (s, 6H, $(CH_3)_2Si$);

$^1$H NMR (200.14 MHz, d6-acetone) δ [lacuna] 6.81 (s, 4H, CH=), 2.17 (m, 2H, $CH_2$—$CF_2$), 1.03 (m, 2H, $CH_2$—Si), 0.40 (t, 6H, J=3.5 Hz, $(CH_3)_2Si$);

$^{13}C${H} NMR (50.33 MHz, d6-acetone) [lacuna] 127.24 (CH=), 125.36 (C=), 117.21 (CH=), 26.52 (t, $^2J_{C,F}$=23.3 Hz, $CH_2$—$CF_2$), 6.77 ($CH_2$—Si), -2.25 ($Si(CH_3)_2$);

$^{19}F${H} NMR (282.35 MHz, d6-acetone) δ [lacuna] -77.04 (t, $J_{F,F}$=9.2 Hz, $CF_3$), -111.52 (m, α-$CF_2$), -117.81 (s, γ-$CF_2$), -118.78 (s, δ-$CF_2$), -119.04 (d, $J_{F,F}$=12.1 Hz, $CF_3$), -122.08 Hz (m, β-$CF_2$);

$^{29}$Si NMR (59.62 MHz, d6-acetone) δ [lacuna] 1.70 ($SiMe_2$).

Elemental analysis calculated for $C_{30}H_{28}Cl_2F_{26}Si_2Zr$; C: 32.73%; H: 2.55%; Cl: 6.45%; F: 44.91%; Si: 5.09%. Found: C: 32.58%; H: 2.56%; Cl: 6.35%; F: 44.78%; Si: 5.39%.

Mass spectrum (ES): molecular mass calculated for $C_{30}H_{28}Cl_2F_{26}Si_2Zr$: 1 100 g/mol. Found: 1 123 g/mol ([M+Na]$^+$).

Preparation of dimethyl(perfluorooctyl) silylcyclopentadiene $C_5H_5Si(CH_3)_2(C_8F_{17})$ 1/Preparation of $HSi(CH_3)_2C_8H_{17}$ [sic] According to the Reaction (3)

50 mmol of butyllithium in 90 ml of hexane are added dropwise over 270 minutes to a mixture, maintained at -78° C., comprising 26.52 g of $C_8F_{17}I$ (48.6 mmol) and 6.8 ml of dimethylchlorosilane in 150 ml of ether.

After having brought the medium to ambient temperature, a white suspension is obtained. 50 ml of water and 150 ml of ether are added.

The mixture is settled, the two layers are separated and the ethereal layer is washed with 30 ml of salt water and then dried over $MgSO_4$.

The solvent is removed on a rotary evaporator; 19.8 g of a yellow oil are obtained, which oil is subjected to distillation under reduced pressure using a 10 cm Vigreux column.

A 10.14 g fraction of $HSi(CH_3)_2C_8F_{17}$ with a boiling point of 57–59° C. under a pressure of 11 mbar and which comprises, according to $^{19}$F NMR, approximately 5% of $C_8F_{17}I$ is obtained (yield: 44%).

$^1$H NMR (300.1 MHz, $CDCl_3$) δ (ppm): 0.38 (d, 6H, $^3J_{H,H}$=4 Hz, $Si(CH_3)_2$), 4.24 (broad, 1H, HSi).

$^{13}C${$^{19}$F} NMR (75.5.1 [sic] MHz, $CDCl_3$) δ (ppm): -7.9 (q, $^1J_{H,C}$=125 Hz, $Si(CH_3)_2$), 108.6, 110.5, 111 (s, 2C), 117.7, 117.4 (t, $^2J_{F,C}$=19 Hz, $CF_3$), 122.7 ($CF_2Si$).

$^{19}$F NMR (282.4 MHz, $CDCl_3$) δ (ppm): -81.9 (t, 3F, $^4J_{F,F}$=9 Hz, $CF_3$), -120.8 (broad s, 2F), -122.6 (broad s, 2F), -122.8 (broad s, 4F), -123.6 (broad s, 2F), -127.1 (broad s, 2F), -127.6 (d, 2F, $^3J_{H,F}$=12 Hz, $CF_2Si$).

$^{29}Si${$^1$H} NMR (59.6 MHz, $CDCl_3$) δ (ppm): -8.3 (tt, $^1J_{H,C}$=125 Hz, $Si(CH_3)_2$), 108.6, 110.5, 111 (s, 2C), 117.7, 117.4 (t, $^2J_{F,Si}$=30 Hz, $CF_3$), $^3J_{F,Si}$=6 Hz [sic].

2/Preparation of $BrSi(CH_3)_2C_8F_{17}$ According to the Reaction (4)

A mixture composed of 7.65 [lacuna] of $HSi(CH_3)_2C_8F_{17}$ (15.8 mmol) and 62 mmol of bromine in 25 ml of $CCl_4$ is stirred at 60° C. for 18 hours. After removing the volatile compounds under reduced pressure, a liquid is obtained and is subjected to flash distillation. 8.35 g of $BrSi(CH_3)_2C_8F_{17}$ are obtained (yield 95%, which exists in the form of a pale pink liquid) [sic].

$^1$H NMR (300.1 MHz, $CDCl_3$) δ (ppm): 0.84 (S); $^{13}C${$^{19}$F} NMR (75.5 MHz, $CDCl_3$) δ (ppm): -0.1 (q, $^1J_{H,C}$=124 Hz, $SiMe_2$), 108.6 (partially resolved q, $J_{H,C}$=12 Hz), 110.4, 111.0 (s, 2C), 111.6, 113.0, 117.4 (t, $^2J_{F,C}$=21 Hz, $CF_3$), 119.3 ($CF_2Si$).

$^{19}$F NMR (282.4 MHz, $CDCl_3$) δ (ppm): 82.0 (t, 3F, $^4J_{F,F}$=9 Hz, $CF_3$), -118.8 (broad s, 2F, $CF_2Si$), -122.5 (broad s, 2F), -122.9 (broad s, 4F), -123.7 (broad s, 2F), -127.2 (m, 4F).

$^{29}Si${$^1$H} NMR (59.6 MHz, $CDCl_3$) δ (ppm): 17.7 (t, $^2J_{F,Si}$=35 Hz).

3/Preparation of $C_5H_5Si(CH_3)_2C_8F_{17}$ According to the Reaction (5)

A solution of 0.93 g of cyclopentadienelithium (12.9 mmol) in 50 ml of THF is added dropwise to a stirred solution of 7.32 g of $BrSi(CH_3)_2C_8F_{17}$ (13.1 mmol) in 50 ml of THF at 0° C. The brown solution obtained is stirred for 1 hour after the end of the addition. The reaction is rapidly halted by addition of 200 ml of water.

Extraction is carried out with 200 ml of pentane and the organic phase is washed with water (2 times with 50 ml) and then with 30 ml of salt water. After drying with magnesium sulphate, the volatile compounds are removed using a rotary evaporator. The liquid obtained is subjected to flash distillation and 5 g of $C_5H_5Si(CH_3)_2(C_8F_{17})$ are obtained (yield: 70%), which exists in the form of a light-yellow liquid.

$^1$H NMR (300.1 MHz, $CDCl_3$) δ (ppm); 0.13 (s, 6H, $SiMe_2$), 0.51 (s, 1.5H, $SiMe_2$), 3.18 (d, 0.4H, J=1.5 Hz, $C_5H_5$), 6.4–7.2 (m, 4.4H, $C_5H_5$).

$^{13}C${$^{19}$F} NMR (75.5 MHz, $CDCl_3$) δ (ppm): -7.6 (q, $^1J_{H,C}$=121 Hz, $SiMe_2$), -5.6 (q, $^1J_{H,C}$=123 Hz, $SiMe_2$), 108.7 (partially resolved q, $J_{F,C}$=12 Hz), 110.5, 111.1 (partially resolved, 2C), 111.8, 113.3, 117.4 (t, $^2J_{F,C}$=16 Hz, $CF_3$), 123.2, 131.7 (unresolved peak), 133.9 (unresolved peak).

$^{19}$F NMR (282.4 MHz, $CDCl_3$) δ (ppm): 81.9 (t, 3F, $^4J_{F,F}$=10 Hz, $CF_3$), -119.2 (broad s, 2F, $CF_2Si$), -122.5 (broad s, 2F), -122.7 (broad s, 4F), -123.6 (broad s, 2F), -126.8 (t, 1.5 F, $^4J_{F,F}$=15 Hz, $CF_2Si$), 127.1 (m, 2F), -127.3 (t, 0.5F, $^4J_{F,F}$=15 Hz, $CF_2Si$).

Preparation of 1,1'-bis[dimethyl(perfluorooctyl) silylcyclopentadienyl]zirconium dichloride $ZrCl_2${$C_5H_4Si(CH_3)_2C_8F_{17}$}$_2$ In a first stage, the lithiated derivative of (perfluorooctyldimethylsilyl)cyclopentadiene is prepared by adding 3.6 ml of n-BuLi (5.7 mmol) in hexane dropwise to a solution composed of 2.77 g of $C_5H_5Si(CH_3)_2C_8F_{17}$ in 50 ml of hexane.

A precipitate slowly forms. The reaction medium is stirred for 12 hours. The precipitate is isolated by centrifuging/separating by settling and is then washed twice with pentane (40 ml and then 25 ml). Drying is carried out under reduced pressure.

2.09 g of Li[C$_5$H$_4$Si(CH$_3$)$_2$C$_8$F$_{17}$] are obtained (yield 75%), which product exists in the form of a white solid.

In a second stage, the metallocene is prepared. 1.26 g of Li[C$_5$H$_4$Si(CH$_3$)$_2$C$_8$F$_{17}$] (2.3 mmol) are cooled to −78° C. and are then suspended at −78° C. in 40 ml of THF.

The mixture obtained, which is blue in colour, is added at −78° C. to a solution of 0.44 g of ZrCl$_4$(THF)$_2$ (1.2 mmol) in 40 ml of THF.

After stirring at −78° C. for 20 minutes, the solution is reheated to ambient temperature and a wine-red solution is obtained. The solution is stirred for 16 hours, during which time the colouring of the solution changes to dark orange.

The THF is removed under reduced pressure and the residue is extracted twice with benzene (40 ml then 20 ml).

After removing the solvent under reduced pressure, 1.05 g of a brown-coloured viscous product are obtained. This product is recrystallized twice from hot toluene. 0.2 g of metallocene of formula ZrCl$_2$\{C$_5$H$_4$Si(CH$_3$)$_2$C$_8$F$_{17}$\}$_2$ is obtained (yield 13%), which product exists in the form of pale yellow needles.

Use of 1,1'-bis[(dimethyl 1H,1H,2H,2H-perfluoro-1-octyl)silylcyclopentadienyl]zirconium [sic] Dichloride, Hereinafter Denoted by CA1, and of the Compound of Formula ZrCl$_2$\{C$_5$H$_4$Si(CH$_3$)$_2$C$_8$F$_{17}$\}$_2$, Hereinafter CA2, in the Polymerization of Ethylene Procedure:

A one litre reactor is dried for 1 hour in an oven at 80° C. under reduced pressure. The reactor is subsequently connected to a polymerization line and then placed successively under nitrogen and under reduced pressure at 130° C. until the pressure reaches 4×10$^{-2}$ mbar. 200 ml of toluene are introduced into the reactor and then ethylene is introduced, under 5 bar when the precatalyst CA1 is used and under 6 bar when the precatalyst CA2 is used. The temperature in the reactor is subsequently stabilized at 80° C. 10 µmol of precatalyst CA1 or CA2 are weighed out in a first flask and the toluene solution of methylaluminoxane (MAO) is weighed out in a second flask in a glove box and these two flasks are closed with a septum. On the polymerization line, toluene (25 ml) is added under nitrogen to the flask comprising the MAO and the solution is injected into the reactor. Subsequently, the same procedure is carried out with the flask comprising the precatalyst. The polymerization lasts for 30 minutes and is subsequently halted with a 2N HCl/ethanol mixture. The polymer obtained is washed twice with acetone and dried at 80° C. for 24 hours in an oven under reduced pressure.

The results are reported in Table 1. The molecular masses Mw and Mn are mean values based on at least two GPC measurements per polyethylene sample.

Results:

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The foregoing references are hereby incorporated by reference.

What is claimed is:

1. A compound of formulae (I) or (II):

in which:

A represents a cyclopentadienyl, indenyl or fluorenyl radical;

R represents a hydrogen atom, a linear or branched alkyl radical having a number of carbon atoms ranging from 1 to 40, an alkoxy radical having a number of carbon atoms ranging from 1 to 10, an aryl radical having from 6 to 20 carbon atoms, an aryloxy radical having from 6 to 10 carbon atoms or an alkenyl radical having a number of carbon atoms ranging from 2 to 10;

Rf represents a perfluoroalkyl radical C$_x$F$_{2x+1}$—(CH$_2$)$_y$— in which x represents an integer ranging from 1 to 20 an y=0, 1, 2 or 3;

n=1, 2 or 3;

z=1, 2 or 3;

B represents a divalent group >MR$^1$R$^2$ or else

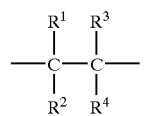

in which M represents a carbon atom, a silicon atom, a germanium atom or a tin atom; R$^1$, R$^2$, R$^3$ and R$^4$, which are identical or different, represent a hydrogen atom, a linear or branched alkyl radical having a number of carbon atoms ranging from 1 to 20 or an aryl radical having from 6 to 14 carbon atoms;

C represents a cyclopentadienyl, methylcyclopentadienyl, pentamethylcyclopentadienyl, butylcyclopentadienyl, indenyl, naphthyl or fluorenyl radical;

w=1 or 2.

2. A compound according to claim 1, wherein in the formulae of which A represents a cyclopentadienyl radical, R represents a methyl radical, Rf represents a perfluoroalkyl

TABLE 1

| Test | Precatalyst | [Zr] (µmol/l) | Molar ratio Al/Zr | Activity (kgPE · mol$^{-1}$[Zr] · h · bar$^{-1}$) | Mw (g · mol$^{-1}$) | Mn (g · mol$^{-1}$) | PI (Mw/Mn) |
|---|---|---|---|---|---|---|---|
| 1 | CA1 | 36 | 545 | 2 000 | 88 000 | 31 000 | 2.8 |
| 2 | CA2 | 40 | 500 | 1 900 | 96 000 | 17 000 | 5.8 | radical $C_xF_{2x+1}(CH_2)_y$— in which x=6 or 8 and y=0 or 2, B=>Si(CH$_3$)$_2$ and w=2.

3. Dimethyl(1H,1H,2H,2H-perfluoro-1-octyl)silylcyclopentadiene.

4. Dimethyl(perfluorooctylsilyl)cyclopentadiene.

5. 1,3-Bis[dimethyl(perfluorooctyl)]silylcyclopentadiene.

6. The compound of formula $(CH_3)_2Si[C_5H_4Si(CH_3)_2C_8F_{17}]_2$.

7. The compound of formula $(CH_3)_2Si[C_5H_3\{Si(CH_3)_2C_8F_{17}\}_2]_2$.

8. Process for the preparation of the compounds of formula (I) $[A][Si(R)_{3-n}RF_n]_z$ according to claim 1 the formulae of which y is other than zero, comprising preparing a lithiated derivative in a nonpolar solvent at a temperature of between 0° C. and 20° C. and in then reacting the said lithiated derivative, dissolved in an ether at low temperature, with a perfluorohalosilane in ethereal solution.

9. Process for the preparation of the compounds of formula (I) $[A][Si(R)_{3-n}RF_n]_z$ according to claim 1 in the formulae of which y=0, comprising:

a) preparing a compound of formula $HSi(R)_{3-n}(C_xF_{2x+1})_n$ from $C_xF_{2x+1}I$, BuLi and $HSi(R)_{3-n}Cl_n$ at low temperature in solvent medium;

b) brominating the said silane $HSi(R)_{3-n}(C_xF_{2x+1})_n$ at a temperature in the region of 60° C. in $CCl_4$, then c) reacting the brominated compound obtained $BrSi(R)_{3-n}(C_xF_{2x+1})_n$ with a lithiated derivative of A.

10. A metallocene of formulae (III) or (IV):

in which:

B represents a divalent group >MR$^1$R$^2$ or else

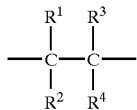

in which M represents a carbon atom, a silicon atom, a germanium atom or a tin atom; R$^1$, R$^2$, R$^3$ and R$^4$, which are identical or different, represent a hydrogen atom, a linear or branched alkyl radical having a number of carbon atoms ranging from 1 to 20 or an aryl radical having from 6 to 14 carbon atoms;

(I') represents a cyclopentadienyl radical having one hydrogen less;

(C') represents a cyclopentadienyl, methylcyclopentadienyl, pentamethylcyclopentadienyl, butylcyclopentadienyl, indenyl or naphthyl radical with one hydrogen less, D=(I') or (C');

M$^1$ represents a metal from Groups III, IVb, Vb or VIb and a metal from the group of the lanthanides or actinides;

L, which is identical or different, represents a halogen atom, a linear or branched alkyl radical having a number of carbon atoms ranging from 1 to 20, an alkenyl radical having from 2 to 20 carbon atoms, an alkoxy radical having from 1 to 20 carbon atoms or an aryloxy or aryl radical having from 6 to 40 carbon atoms;

t represents an integer ranging from 1 to 4 and is equal to 2 when, in the formulae (III) and (IV), M$^1$=Ti, Zr or Hf; w=1 or 2.

11. A metallocene according to claim 10, wherein in formula (IV):

M$^1$=Zr,

L=Cl, t=2

(I')=$(CH_3)_2Si[C_5H_4Si(CH_3)_2(CH_2)_2(CF_2)_5CH_3]$ or $(CH_3)_2Si[C_5H_4Si(CH_3)_2C_8F_{17}]$;

B=$(CH_3)_2Si<$.

12. Process for the production of polyolefins by polymerization of at least one olefin in the presence of a catalyst comprising a compound of formula (III) or (IV) from claim 10 and at least one cocatalyst.

13. Process according to claim 12, wherein the cocatalyst is an aluminoxane.

14. Process according to claim 13, wherein the aluminoxane is methylaluminoxane (MAO).

15. Process according to claim 12, wherein the olefin has the formula R$^\alpha$—CH=CH—R$^\beta$, in which R$^\alpha$ and R$^\beta$, which are identical or different, represent a hydrogen atom, a halogen atom, a linear or branched hydrocarbon radical having a number of carbon atoms ranging from 1 to 20 or a phenyl radical optionally substituted by a halogen atom or a linear or branched alkyl radical having a number of carbon atoms ranging from 1 to 4.

16. Process according to claim 15, wherein the olefin R$^\alpha$—CH=CH—R$^{62}$ is ethylene.

17. Process according to claim 15, wherein the hydrocarbon radical contains from 1 to 10 carbon atoms.

* * * * *